United States Patent
Palfy et al.

(10) Patent No.: US 8,002,897 B2
(45) Date of Patent: Aug. 23, 2011

(54) AT-HOME INTEGRATED CLEANING AND DISINFECTION SYSTEM AND METHOD FOR DENTAL HARDWARE

(75) Inventors: Valerie Palfy, Paoli, PA (US); Don A. Skomsky, West Chester, PA (US)

(73) Assignee: Integrity Engineering, Inc, West Chester, PA (US)

( * ) Notice: Subject to any disclaimer, the term of this patent is extended or adjusted under 35 U.S.C. 154(b) by 0 days.

(21) Appl. No.: 12/803,401

(22) Filed: Jun. 26, 2010

(65) Prior Publication Data

US 2010/0269861 A1 Oct. 28, 2010

Related U.S. Application Data

(62) Division of application No. 10/322,648, filed on Dec. 19, 2002, now Pat. No. 7,798,159.

(51) Int. Cl.
*B08B 3/12* (2006.01)
(52) U.S. Cl. ............. 134/1; 134/25.1; 134/25.4; 134/34
(58) Field of Classification Search ................. None
See application file for complete search history.

(56) References Cited

U.S. PATENT DOCUMENTS

| | | |
|---|---|---|
| 3,478,758 A | 11/1969 | Davies |
| 3,852,032 A | 12/1974 | Urbach |
| 3,955,922 A | 5/1976 | Moulthrop |
| 4,063,890 A | 12/1977 | Baron |
| 4,114,194 A | 9/1978 | Walter |
| 4,366,125 A | 12/1982 | Kodera et al. |
| 4,448,705 A | 5/1984 | Gray |
| 4,448,750 A | 5/1984 | Fuesting |
| 4,698,206 A | 10/1987 | Nevin |
| 4,746,489 A | 5/1988 | Arnold |
| 4,868,397 A | 9/1989 | Tittel |
| 5,120,499 A | 6/1992 | Baron |
| 5,144,144 A | 9/1992 | Borovsky |
| 5,166,528 A | 11/1992 | Le Vay |

(Continued)

FOREIGN PATENT DOCUMENTS

DE 4310264 A1 10/1994

(Continued)

OTHER PUBLICATIONS

PuriLens, "Abstracts and Articles," Dec. 11, 2002.

(Continued)

*Primary Examiner* — Michael Barr
*Assistant Examiner* — Ryan Coleman

(57) ABSTRACT

An at-home integrated cleaning and disinfection system for dental hardware, for consumer use includes a compact and portable base unit sized for at-home use by a consumer, the base unit including a holding frame and an ultraviolet lamp. The system also includes a cleaning chamber within which dental hardware and a cleaning solution that includes hydrogen peroxide are receivable. The cleaning chamber fits within the holding frame in a manner such that contents of the cleaning chamber are exposed to light emitted by the ultraviolet lamp. A vibration mechanism is positioned so as to cause the cleaning chamber to vibrate while the cleaning chamber is fitted within the holding frame. To clean and disinfect dental hardware, the consumer places dental hardware in the cleaning chamber, fills the cleaning chamber with the cleaning solution, and inserts the cleaning chamber into the holding frame. The vibration mechanism is activated, so as to cause the cleaning chamber to vibrate while the cleaning chamber is fitted within the holding frame, and the ultraviolet lamp is activated, so as to expose contents of the cleaning chamber to light emitted by the ultraviolet lamp.

20 Claims, 5 Drawing Sheets

U.S. PATENT DOCUMENTS

| | | |
|---|---|---|
| 5,184,633 A | 2/1993 | Langford |
| 5,185,532 A | 2/1993 | Zabsky et al. |
| 5,225,172 A | 7/1993 | Meyler et al. |
| 5,316,591 A | 5/1994 | Chao et al. |
| 5,534,741 A | 7/1996 | Smith |
| 5,547,584 A | 8/1996 | Capehart |
| 5,628,971 A | 5/1997 | Norman |
| 5,630,436 A | 5/1997 | Chase |
| 5,744,094 A | 4/1998 | Castberg et al. |
| 5,759,540 A | 6/1998 | Nielsen |
| 5,823,016 A | 10/1998 | Glotz |
| 5,853,290 A | 12/1998 | Winston |
| 5,975,094 A | 11/1999 | Shurtliff |
| 5,996,155 A | 12/1999 | Chao et al. |
| 5,997,812 A | 12/1999 | Burnham et al. |
| 6,007,686 A | 12/1999 | Welch et al. |
| 6,039,921 A | 3/2000 | Boucher |
| 6,181,052 B1 | 1/2001 | Puskas |
| 6,183,705 B1 | 2/2001 | Chang |
| 6,239,442 B1 | 5/2001 | Iimura |
| 6,361,610 B1 | 3/2002 | Scotto et al. |
| 2002/0098139 A1 | 7/2002 | Sparks |
| 2004/0259971 A1 | 12/2004 | Sasa |

FOREIGN PATENT DOCUMENTS

| | | |
|---|---|---|
| EP | 638523 A1 | 2/1995 |

OTHER PUBLICATIONS

Kenneth Shay, "Denture Hygiene: A Review and Updated," the Journal of Contemporary Dental Practice, vol. 1, No. 2, pp. 1-8, 2000.

SkyMall, Inc., "Antibacterial Toothbrush Purifier Takes Oral Hygiene to the Next Level!" 2002.

Solarchem Environmental Systems, "The UV/Oxidation Handbook," pp. 1-1, 2-1, 2-4, 2-5, and 2-6, 1994.

Tactica International, "Delta-Sonic Dental Cleaner," Oct. 2002.

Gina White, "Caring for Soft Contact Lenses," AllAboutVision.com, Dec. 11, 2002.

Hartman et al., Synergistic Killing of *Escherichia coli* by near-UV radiation and hydrogen peroxide, Journal of Bactareology, V. 133, No. 2, pp. 769-774, 1978.

Bayliss et al., The effect of hydrogen peroxide and ultraviolet irradiation on non-sporing bacteria, Journal of Applied Bacteriology, v. 48, pp. 417-422, 1980.

FIG. 1A
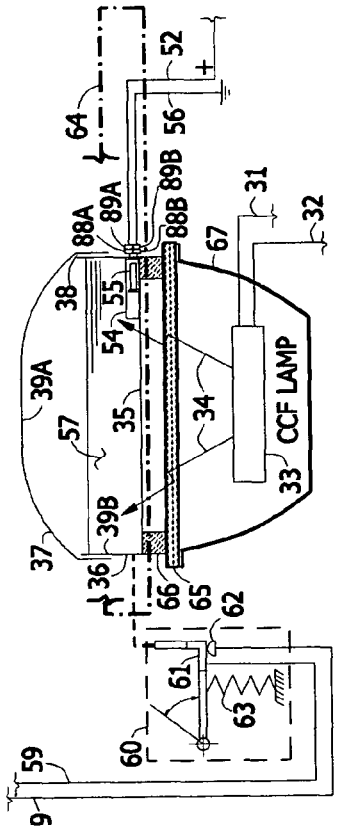
OPTION 1
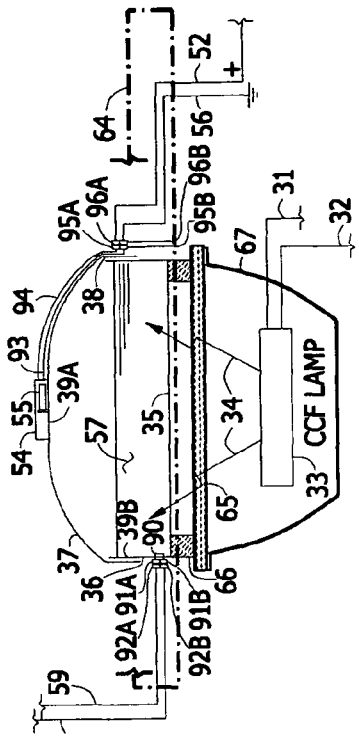
OPTION 3
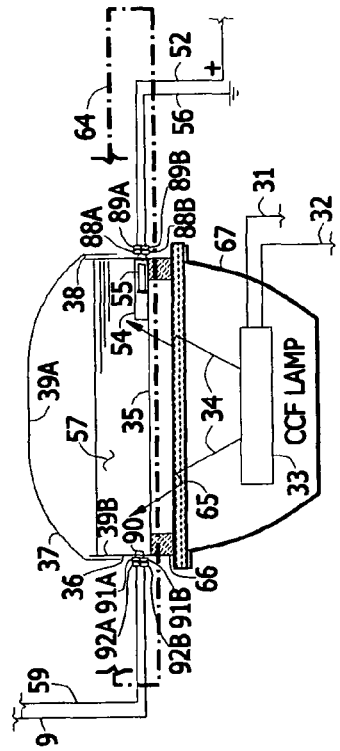
OPTION 2

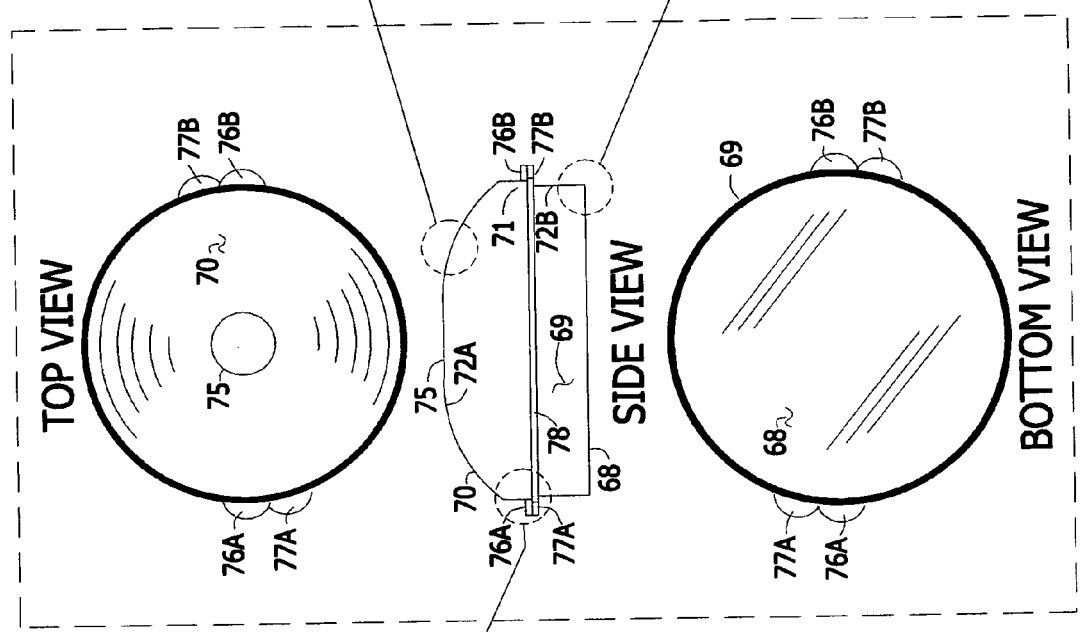

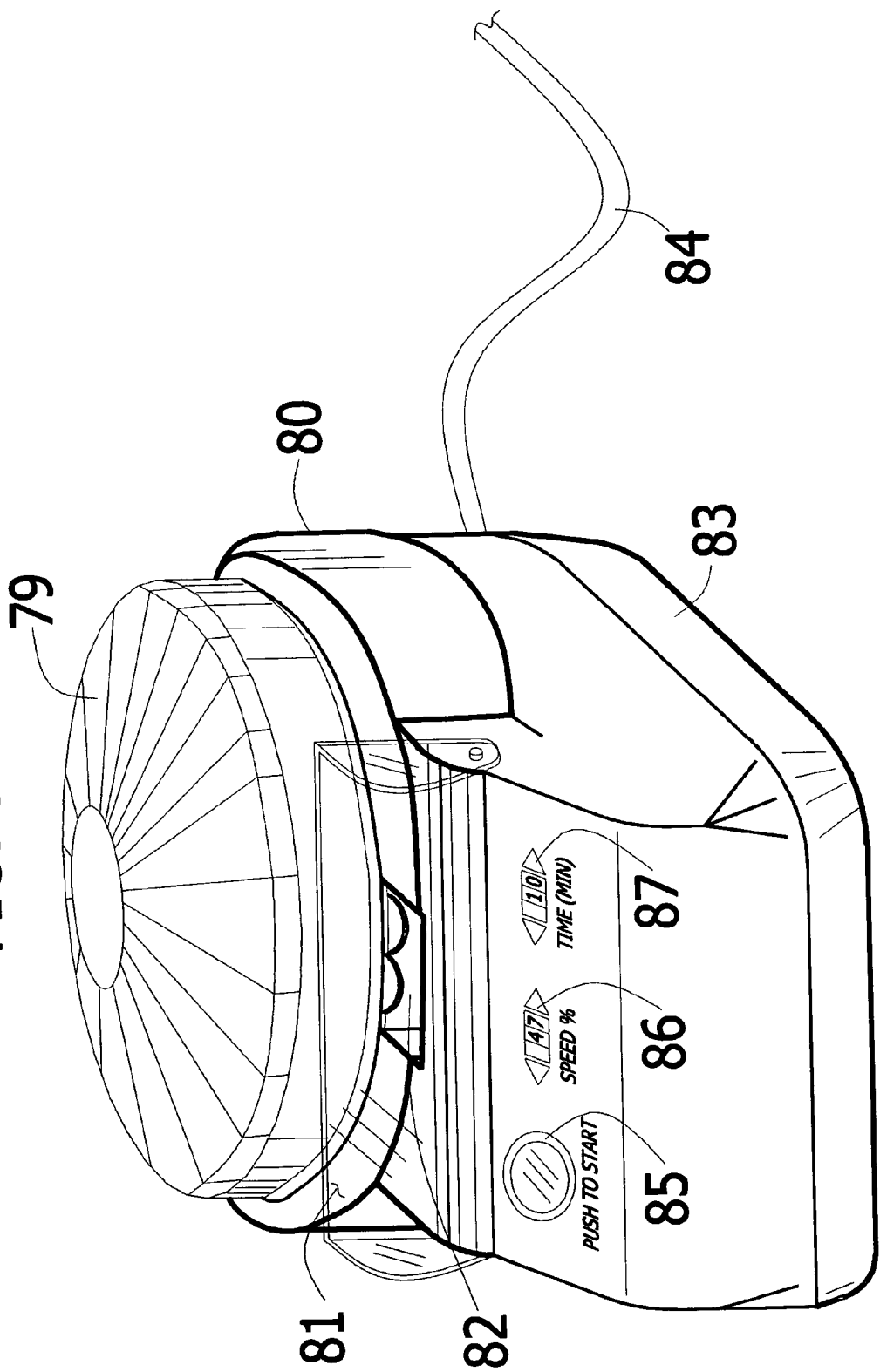

AT-HOME INTEGRATED CLEANING AND DISINFECTION SYSTEM AND METHOD FOR DENTAL HARDWARE

This is a divisional application of U.S. patent application Ser. No. 10/322,648, filed Dec. 19, 2002 now U.S. Pat. No. 7,798,159, the entire disclosure of which is hereby incorporated herein by reference.

TECHNICAL FIELD

This invention relates to at-home systems and methods for cleaning and disinfecting dental hardware, such as prostheses, dentures, plates, retainers, clips, and removable implants, for consumer use, and more particularly to systems and methods that employ immersion of these hardware in a liquid, and thereafter vibration of the liquid, either subsonically, sonically, or ultrasonically, combined concurrently with exposure of hydrogen peroxide in the liquid to ultraviolet light.

BACKGROUND

Traditional at-home cleaning techniques for dental hardware include brushing by hand or placing the hardware in a solution with tablets that acidify and effervesce. Such tablets may be comprised of, for example, an inorganic bleach, sodium perborate, with a coloring agent, preservatives, flavor, and a catalyst or two. When sodium perborate is placed in water, it reacts to form a mild solution of hydrogen peroxide, while releasing oxygen. These techniques for cleaning hardware can also reduce the potential for odor to the extent that they destroy bacteria.

The methodology of employing ultra-high frequency sound waves or mechanical movement as a means to impart low-amplitude motion to objects or fluids for dislodging particulate matter has been known for many years. The basic equipment for this technique includes a power generating unit and one or more piezoelectric crystals-elements or electromechanical motors. Vibration of the piezoelectric crystal-element is accomplished when direct current (DC) is applied across the piezoelectric crystal. Once electrically polarized, the crystal deforms axially in the direction of the polarization. If the electrical current is halted and then reverse biased, the crystal returns first back to its null position and proceeds to deform to the same magnitude in the opposite direction along a single linear axis. If the current is repeatedly applied and then reversed, the crystal, and hence the piezoelectric element, will oscillate back and forth along a single axis at the frequency of the reversing applied current.

The normal range of human hearing is between 20 and 20,000 cycles per second (CPS, Hertz, or Hz). Vibratory motion of solids or fluids below 20 Hz is below the threshold of human hearing and is defined as being subsonic. Vibratory motion within the 20 Hz to 20,000 Hz band is within the range of human hearing and is, by definition, sonic. Vibratory motion above the 20,000 Hz threshold is considered to be in the ultrasonic range, or that which is beyond the ability of human hearing. Thus, for example the application of reversing current at a frequency of 20,000 Hz or greater to a piezoelectric crystal-element will generate linear oscillatory motion in the low ultrasonic region. If the piezoelectric crystal-element is surrounded by relatively inviscid fluid in a container, the oscillatory motion will be transferred to the fluid, and standing waves of a peak-to-peak period, in seconds, of $1/2\pi$ times the applied current frequency will result. The amplitude of the standing waves is increased by increasing the applied voltage to the crystal-element. Thus, cyclic motion of the inviscid fluid may be generated to the degree desired by establishing the frequency of electrical stimulation and the voltage applied to the piezoelectric crystal-element.

Being in motion relative to any large body submerged within it, the fluid imparts molecular agitation to the body's exterior surface or surfaces, along with all particulate matter that is mechanically attached to it. With repeated exposure to the agitated fluid, these particulates will become dislodged over time. In such a manner, a cleaning effect of the body occurs, to the extent that, in general terms, particles that are beyond the physical reach of mechanical brushes or removal tools can be dislodged by the motion of the fluid bath.

Similar ultrasonic motion may be generated by electromechanical means by using a small single-pole or multi-pole, direct-current or alternating-current motor, onto whose rotor one or more eccentric weights have been affixed, or, alternately, onto whose rotor eccentric weight has been removed. The rotor is thus in a dynamically unbalanced state when rotated, due to the inertial force of the weight, or absence of it, as the rotor is rotated in a circular path. This inertial imbalance, formed over a two-dimensional plane perpendicular to the rotor's axis, is transferred through the motor's bearings and into its stator and mounting frame. Thus, for example, with the application of the correct DC voltage to the unbalanced motor to achieve a rotational speed in excess of 20,000 RPM, vibratory motion of the motor itself in the low ultrasonic frequency range (20,000 Hz) can be achieved. The amplitude of the vibratory motion is governed by the quantity and radial position of the weight imbalance in the rotor and the DC voltage applied to the motor windings. If surrounded by a relatively inviscid fluid in a container, as was the case with the piezoelectric crystal-element previously described, oscillatory motion of that fluid will result. However, due to the fact that the inertial force of the motor's rotor imbalance is directed in a plane rather than a single line, the amount of physical motion imparted to the fluid typically is comparatively greater than that produced by a piezoelectric crystal. Motion can be imparted in a manner such that the vector of fluid momentum continually changes direction, repeating a 360-degree cycle with each revolution of the rotor. Thus, a body submerged in a vibrating fluid bath will experience a cleaning effect, due to the repetitive impact of fluid molecules onto the body's surface.

Patents describing systems that employ high-frequency movement and relative motion, piezoelectric crystals-elements or unbalanced DC motors, and aqueous solutions and baths for imparting ultrasonic cleaning include Smith, U.S. Pat. No. 5,534,741 and Puskas, U.S. Pat. No. 6,181,052. U.S. Pat. No. 5,534,741 describes in some detail a timed piezoelectric ultrasonic device and residence tank for cleaning jewelry. A piezoelectric element is pulsed so as to effect cleaning of the jewelry by varying and increasing the agitation of a solution bath in which it is submerged. The device described in U.S. Pat. No. 6,181,052 is similar to that of U.S. Pat. No. 5,534,741 in that an ultrasonic transducer (in the case of U.S. Pat. No. 6,181,052, three transducers) creates ultrasonic motion of a fluid bath into which an object is placed, thus effecting cleaning of that object. The device is intended for use with unidentified "delicate parts." The frequency of oscillations is intentionally varied to cause physical dislodging of particulates attached to an object immersed within the bath tank.

Winston, U.S. Pat. No. 5,853,290 is representative of techniques in which a tool is ultrasonically vibrated to dislodge particles from an object, such as a tooth, that cannot be physically removed and placed within a liquid bath. An ultrasonic element is used to agitate fluid enclosed within a hermetically sealed flexible tube, onto the end of which the tool itself is affixed. The ultrasonic vibration of the liquid, and hence the tool, is accomplished by a remotely mounted power generating unit to which the liquid-filled tube is affixed. Thus, once energized, the tool may be positioned in any orientation or position, while axial ultrasonic vibration of the tool head continues unabated.

In the above-described systems, cleaning of the body in question is performed via the agitation of a liquid bath surrounding that body, this agitation being lineally transferred from an axially vibrating element to the liquid itself.

In accordance with advances in technology, liquid baths and the object or objects being cleaned may be subjected to direct ultraviolet (UV) radiation, so as to effect irradiative sterilization action. One or more direct-acting antibacterial chemicals in the bath may also be used, to effect chemical sterilization action concurrently with the irradiative action. Ultrasonic cleaning by piezoelectric or like means may also be incorporated.

Fuesting, U.S. Pat. No. 4,448,750 improves upon the generalized ultrasonic cleaning technique by the addition of an ultraviolet bulb in the device that irradiates a liquid bath from above with light at a preferred wavelength of 2537 angstroms (253.7 nanometers), for the purpose of concurrently cleaning and sterilizing medical and dental instruments. This patent also prescribes the content of the cleaning-sterilizing fluid, and in particular those constituents in water that would offer the best transmittance of the UV radiation from the bulb through the fluid and onto the item or items being cleaned and sterilized. Hydrogen peroxide ($H_2O_2$) is specifically excluded as a preferred constituent or additive to the bath because, according to the patent, the transmittance of $H_2O_2$ to UV radiation is less than 1 percent, while the desired transmittance of the liquid solution to ultraviolet radiation should be greater than twenty percent. Thus, the intent is to effect sterilization of an item by direct contact of the item with the solution bath, concurrently with direct UV irradiation of the item, and not as an indirect consequence of UV absorption by the cleaning solution itself. The dental instruments shown in the Fuesting patent appear to be of the type commonly used in dentist's offices, which frequently cause bleeding of gums. Thus, sterilization is of particular importance to avoid infection to the patient through the patient's blood system.

The apparatus of the Fuesting patent, which is a modified version of a relatively large and bulky and commercially available ultrasonic bath, is intended for use in a dentist's office or similar environment. Because of its size and relatively non-portable construction, the apparatus does not lend itself to at-home use by consumers. Because the fluid-filled cleaning chamber occupies the entirety of the base of the apparatus, the entire apparatus must vibrate during use and, furthermore, the cleaning chamber cannot be removed from the rest of the apparatus or serve as a portable storage container. Rather, it appears that the medical or dental practitioner must retrieve the individual medical or dental instruments, or a tray carrying multiple instruments, from the inside of the base of the apparatus. Although the Fuesting patent mentions that the top cover of the apparatus can be lined with reflective material, it seems that a certain percentage of the ultraviolet radiation would be dispersed in the form of heat.

$H_2O_2$ irradiated by UV light results in the near-complete absorption of the UV light, leading to molecular photolysis of $H_2O_2$ into constituent hydroxyl (OH) radicals. The chemical interaction of these free, and extremely aggressive, hydroxyl radicals with bacteria and viruses causes the destruction of these pathogens by altering, among other things, their DNA structures. Once chemically altered by the OH radicals, these pathogens either die immediately or quickly mutate such that they cannot replicate, in effect dying shortly afterwards. Thus, although $H_2O_2$ is an effective biocide by itself, and UV irradiation is effective in killing bacteria and viruses by itself the combination of $H_2O_2$ irradiated by UV light can produce a far greater biocidal effect due to photolysis and the creation of sterilizing hydroxyl free radicals. The biocidal effect also has been found to be useful for the remediation and cleanup of water containing hazardous levels of dissolved organic materials.

Baron, U.S. Pat. No. 5,120,499 describes a small, compact system for asepticizing contact lenses, in which the contact lenses are placed in a weak solution of hydrogen peroxide (no greater than 30 parts per million) and exposed to ultraviolet radiation from an ultraviolet source behind which a reflector is mounted. Ultrasonic vibration of the lenses is employed to cause dislodgement of microorganisms from the lenses, but the patent does not state that the ultrasonic vibration is used as the cleaning method for the lenses (such that traditional cleaning or rinsing would not be required). The background section of the Baron patent indicates that prior asepticization techniques, such as chemical treatment, were focused primarily on preventing damage to the contact lenses themselves rather than preventing infection of the eyes or of other parts of the human body by exposure of the eyes to micro-organisms (direct contact of eyes with micro-organisms being a very common cause of infection). The contact lens receptacle tray is not suitable for receiving dental hardware.

SUMMARY

The invention provides an at-home integrated cleaning and disinfection system for dental hardware, for consumer use. As used herein and in the claims, the term "at-home" means sized and configured for use in home environments such as bathrooms or nightstands, even if actual use occurs in other environments such as hotels or dentist's offices. Furthermore, the recitation of "dental hardware" herein and in the claims should not be construed as excluding dual-purpose systems that, in addition to being suitable for cleaning and disinfecting dental hardware, are also suitable for cleaning other items such as jewelry, tattoo needles, cosmetology devices, etc. at the option of the consumer.

The system includes a compact and portable base unit sized for at-home use by a consumer, the base unit including a holding frame and an ultraviolet lamp. The base unit may also include electronics and controls for the system. The system also includes a cleaning chamber within which dental hardware and a cleaning solution that includes hydrogen peroxide are receivable. The cleaning chamber fits within the holding frame in a manner such that contents of the cleaning chamber are exposed to light emitted by the ultraviolet lamp. A vibration mechanism is positioned to cause the cleaning chamber to vibrate while the cleaning chamber is fitted within the holding frame.

To clean and disinfect dental hardware, the consumer places the dental hardware in the cleaning chamber and fills the cleaning chamber with the cleaning solution. The vibration mechanism is activated, to cause the cleaning chamber to vibrate while the cleaning chamber is fitted within the holding frame, and the ultraviolet lamp is activated, to expose contents of the cleaning chamber to light emitted by the ultraviolet lamp.

In certain embodiments of the invention, after the consumer places the dental hardware in the cleaning chamber and fills the cleaning chamber with the cleaning solution, the consumer closes the container and places it within the holding frame before the vibration mechanism and the ultraviolet lamp are activated.

The cleaning and disinfection system constructed in accordance with the invention, with its compact and portable base unit and cleaning chamber that fits within a holding frame of the base unit, allows the consumer conveniently to perform subsonic, sonic, or ultrasonic cleaning and UV peroxidation of dental hardware at home or at any other location desired by the consumer. It is not necessary for the consumer to take the dental hardware into a dental office or similar environment to be cleaned and disinfected by specialized equipment. Of course, while the cleaning and disinfection system of the invention is designed with home use in mind, it may be used by dentists, orthodontists, and other specialists too.

The subsonic, sonic, or ultrasonic cleaning can be more convenient and effective than other at-home cleaning techniques such as brushing by hand or placing the hardware in a solution with tablets that acidify and effervesce. In particular, the mechanical cleaning action of the inventive technique need not require brushing to ensure that all particulates are dislodged, and need not require rinsing to prevent ingestion of chemical residue created by tablets and to assist with removal of particulates not removed by tablets. For example, the invention can eliminate any need for elderly or frail users of dental hardware to perform brushing tasks, handling of tablets, and rinsing of the dental hardware and cleaning chamber, and children need not be monitored to ensure that such tasks are performed thoroughly and correctly or to ensure that the tablets are not swallowed, which might cause chemical burns. The invention can allow the cleaning and disinfection process to be stopped conveniently at any point in time, in contrast to tablet-based cleaning systems. Furthermore, the invention can enable the dental hardware to be cleaned in as little as five minutes (which the consumer can lengthen at will to enhance effectiveness), whereas a typical tablet-based system might require about fifteen minutes. The invention can provide a sealed, leak-proof system that can be used easily on airplanes and similar environments, unlike oxygen-releasing tablets that require open containers to allow oxygen to escape or require specially constructed drainage systems. The consumer need not use warm water for cleaning. It is not necessary for the consumer to keep purchasing effervescent tablets, which can be expensive. Rather, the consumer incurs a one-time cost upon purchasing the system.

A primary biocidal action is caused by dissociation of hydrogen peroxide molecules into free hydroxyl radicals upon absorption of ultraviolet light by the hydrogen peroxide molecules, the free hydroxyl radicals in turn chemically attacking and killing bacterial and viral cells. This biocidal action can be more effective than the use of hydrogen peroxide alone or the use of UV irradiation alone. Nevertheless, a secondary biocidal action may be caused by direct irradiation of bacterial and viral cells by ultraviolet light, and a tertiary biocidal action may be caused by hydrogen peroxide chemical attack on bacterial and viral cells.

Thus, while the human mouth may not be nearly as susceptible to infection as the eyes or reparatory system, the ultraviolet peroxidation technique of the invention can nevertheless provide a highly effective disinfection system that accommodates consumer perception that dental prostheses, retainers, and the like ought to be sterilized more thoroughly than can be accomplished by ordinary techniques for cleaning dental hardware (even if that perception is inconsistent with the consumer's use of toothbrushes, foods, cigarettes, etc.). The invention can combine up to three disinfection components (UV peroxidation, ultraviolet radiation alone, and free radical attack) to provide highly thorough sterilization.

In one embodiment of the invention, the base unit, with the cleaning chamber fitted within the holding frame of the base unit, may be about 5 and ½ inches tall; 3 and ½ inches wide; and 4 inches deep. The construction is highly convenient for allowing consumers to clean and disinfect prostheses, dentures, plates, retainers, clips, removable implants, and other dental hardware automatically in a bathroom or on top of a nightstand (and possibly for allowing consumers to clean and disinfect other items such as jewelry or tattoo needles in addition to dental hardware, at the option of the consumer).

The cleaning chamber may be removable from the holding frame of the base unit, and may serve as a portable storage container for the dental hardware. Thus, the consumer need not remove the dental hardware from the solution of the cleaning and disinfection system until the consumer is actually ready to use the hardware. Nor is there ever a need to move the dental hardware from the cleaning and disinfection system into a distinct storage container.

The cleaning chamber may include a transparent window through which ultraviolet light is transmitted from the ultraviolet lamp to the cleaning solution. This transparent window can allow viewing of the dental hardware by the consumer when the cleaning chamber is removed from the holding frame. Thus, the consumer can see the condition of the dental hardware, including the extent to which it has been cleaned, without removing the dental hardware from the cleaning solution.

The ultraviolet lamp of the base unit may be positioned beneath the cleaning chamber, and the holding frame of the base unit may be a housing that surrounds the cleaning chamber circumferentially, while the cleaning chamber is fitted within the holding frame of the base unit. This arrangement can allow the cleaning chamber to be fitted conveniently into the top of the base unit for ease of use by the consumer.

At least a portion of the base unit may be mechanically isolated from vibration. This isolation from vibration can be important to the consumer when the base unit is used in a bathroom or on a nightstand, and helps to protect the electrical circuitry and the ultraviolet lamp.

The vibration mechanism may be a micro-motor such as a multi-pole, direct current, eccentrically unbalanced micro-motor. Such a micro-motor can produce three-dimensional, rather than two-dimension, motion within the cleaning solution, thereby enhancing the effectiveness of the cleaning process, and can efficiently produce a relatively large amount of motion in the cleaning solution given the size of the micro-motor.

The vibration mechanism may be operatable at consumer-selectable frequencies, and the vibration mechanism may be wired to operate for a consumer-selectable time. These features can allow the consumer to experiment with different frequencies and times in order to find the frequency and/or time that works best for cleaning the dental hardware, or that is preferred by the consumer for any other purpose such as minimizing undesirable noise.

Similarly, the ultraviolet lamp may be wired to operate for a consumer-selectable time, and a timer may be provided with which a time duration of operation of the vibration mechanism and the ultraviolet lamp is selectable by the consumer, thereby providing additional flexibility to the consumer in operating the system.

The ultraviolet lamp may be a cold cathode fluorescent lamp. Internal reflectors may be provided in both the base unit as well as the cleaning chamber to reflect ultraviolet light into the cleaning solution. The use of a cold cathode fluorescent lamp, and the use of reflectors in both the base unit as well as the cleaning chamber to reduce losses of the ultraviolet radiation, can avoid substantial heating of the cleaning and disinfection system, thereby enhancing suitability of the system for use by consumers at home and avoiding any damage, such as melting, to the dental hardware. The internal reflectors may substantially surround the combination of the ultraviolet lamp and the cleaning solution to ensure that as much of the ultraviolet light as possible interacts with the hydrogen peroxide in the cleaning solution. This arrangement can reduce the amount of time that the consumer must wait for disinfection to be completed, and can allow portions of the cleaning and disinfection system to be translucent without risk of exposing the consumer to potentially hazardous ultraviolet light.

At least one mechanical switch may be positioned to sense whether the cleaning chamber is properly fitted within the holding frame of the base unit, and may be wired to prohibit activation of the ultraviolet lamp and the vibration mechanism unless the cleaning chamber is properly fitted within the holding frame. This feature enhances the safety of the system to ensure that an absent-minded or careless consumer does not use the system incorrectly by attempting to operate it while the cleaning chamber is not properly fitted within the holding frame, which might result in exposure of the user to ultraviolet radiation.

The vibration mechanism and the ultraviolet lamp may be wired to be activated simultaneously, so that cleaning and disinfecting occur simultaneously. Thus, both functions are performed conveniently and automatically at home by a single integrated system.

Specific embodiments of the invention described in detail below provides a convenient and practical means to concurrently destroy various bacteria and viruses on and about the prosthetic itself, through photolysis of hydrogen peroxide and direct chemical and narrow-spectrum light irradiation means, while removing particulate matter via ultrasonic agitation of the solution bath. Narrow-spectrum irradiation light is generated by a cold cathode fluorescent lamp (CCFL) while agitation of the solution bath is accomplished by a variable-speed micro-motor that vibrates the container within which the dental hardware and solution are placed. The container and surrounding fixture are mechanically isolated via an elastomer such that only the holding fixture and container are irradiated and excited by vibration. In addition, the device contains an electronic timer such that, once initiated, the process of cleaning and disinfecting continues until a pre-established time duration has expired. At this point, the process is automatically halted, permitting the user to remove and thereafter don the cleaned and disinfected dental hardware.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a diagram depicting three alternative options for a portion of the electrical circuitry of FIG. 1.

FIG. 2 is a drawing of the top, side, and bottom of a dental hardware cleaning chamber in accordance with the invention.

FIG. 2A is a cross-sectional drawing of a portion of the cleaning chamber upper section of FIG. 2.

FIG. 2B is a cross-sectional drawing of a portion of the cleaning chamber lower section of FIG. 2.

FIG. 2C is a cross-sectional drawing of a portion of the cleaning chamber upper and lower sections of FIG. 2, providing details of their juxtaposition in establishing a leak-tight friction fit.

FIG. 3 is a drawing of a fully assembled cleaning and disinfection device in accordance with the invention.

Like reference symbols in the various drawings indicate like elements.

DETAILED DESCRIPTION

Figure 1:
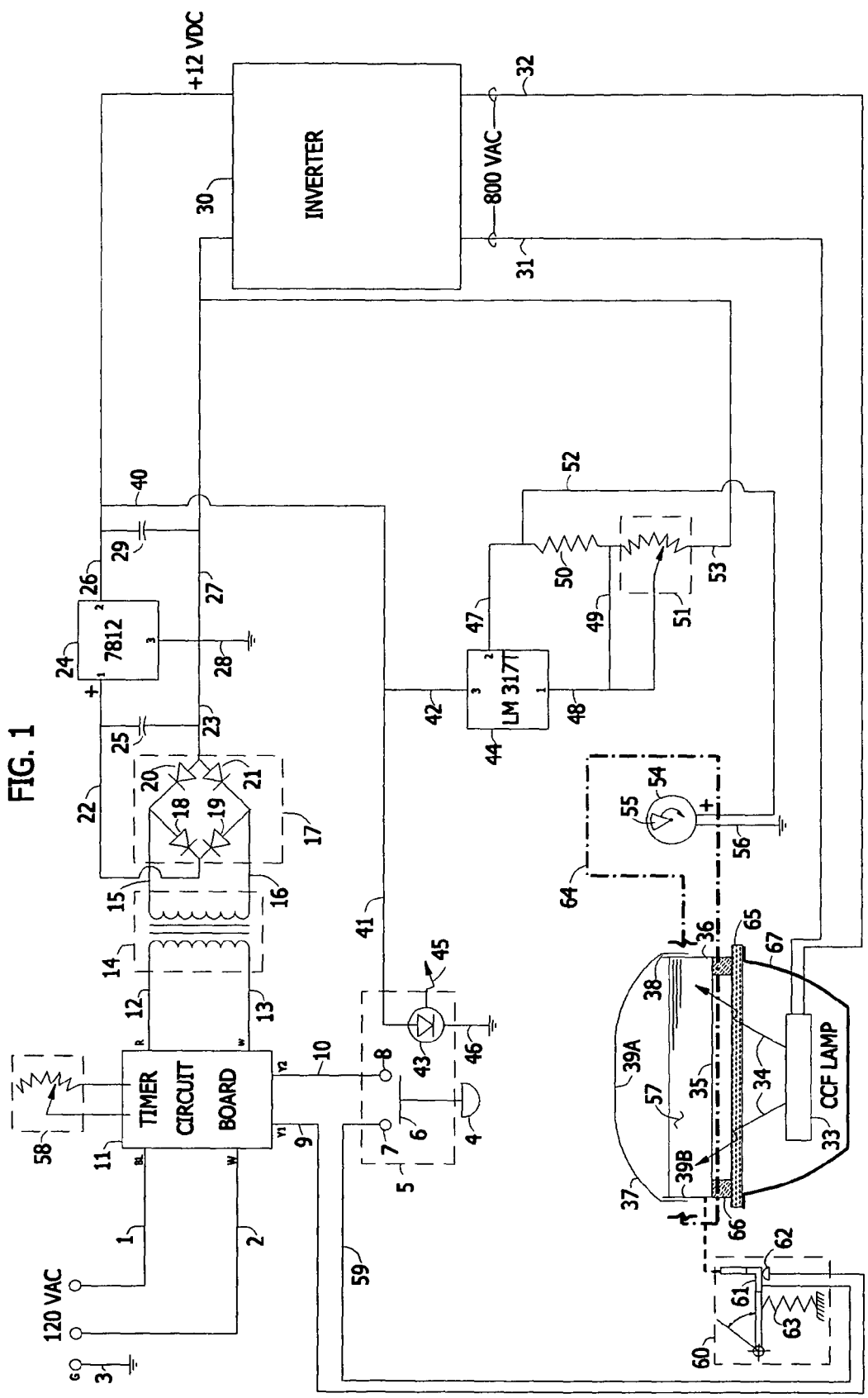
FIG. 1 is a circuit diagram of the electrical circuitry for a dental hardware cleaning and disinfection device in accordance with the invention.

With reference to FIG. 1, devices and methods for concurrently cleaning and disinfecting dental hardware (such as prostheses, dentures, plates, retainers, clips and removable implants) utilizing UV peroxidation and subsonic, sonic, and ultrasonic vibration according to the invention include the following electrical circuitry, which is supplied with main power by conductors 1 and 2, having a ground conductor 3. Nominal 120-volt, 1-phase AC power is supplied by these conductors to a timer circuit board 11, which includes, in part, a momentary contact pushbutton switch 5 and switch assembly 60. Energization of the device is initiated by depressing the pushbutton switch button 4, causing contact element 6 to bridge across contact pins 7 and 8. As a safety feature, switch assembly 60 is electrically incorporated in a series arrangement in this switching circuit, such that energization of the device cannot occur unless the cleaning chamber, comprised of a lower section 36 and an upper section 37 (see also FIGS. 2, 2A, 2B and 2C), is correctly inserted in a vibratable holding frame 64 (more specifically, a vibratable solid housing) of the cleaning device. For illustrative purposes, switch 60 is depicted as a mechanical device, but may incorporate other switching methodologies, including but not limited to magnetic switches, reed switches, capacitive switches, etc. When the cleaning chamber is correctly positioned in the device, switch 60 is closed by the movement of contact element 61 (which is electrically connected to contact pin 7 through conductor 59) making contact with contact pin 62, completing the electrical circuit through conductors 9 and 10. Switch 60 contains a spring 63, which returns the contact element 61 to a non-contact position when the cleaning chamber is not inserted in the cleaning device housing An additional element of the timer circuit board 11 is variable resistor 58. This element, illustrated schematically as a mechanical device but which may be comprised of an electronic device to accomplish the same result, is user-changeable and sets the time during which the timer circuit board remains energized.

Once energized, timer circuit board 11 permits 120-volt, 1-phase AC power to be directed for a specific period of time through conductors 12 and 13 to a step-down transformer 14, and thereafter to an AC-to-DC voltage rectifier 17 through conductors 15 and 16. Rectifier 17, comprised of diodes 18, 19, 20, and 21, converts the transformed AC voltage into a fully rectified DC voltage source. Capacitor 25 is incorporated into the electrical circuit to provide filtering of the rectified source across output conductors 22 and 23.

Thereafter, the rectified DC source is directed to a DC-to-DC voltage regulator 24. Voltage regulator 24 converts the voltage supplied by conductors 22 and 23 into 12-volts DC, being available to energize further elements through conductors 26 and 27. Conductor 28 serves to ground the device while capacitor 29 installed across conductors 26 and 27 provides final filtering of the regulated voltage.

Conductors 26 and 27 branch thereafter, subsequently providing power to three additional electrical circuit assemblies. Inverter 30 is supplied power directly by conductors 26 and 27, converting the 12-volt DC supply to single-phase AC at a voltage of approximately 800 VAC. This AC voltage is directed through conductors 31 and 32 to energize a cold cathode fluorescent (CCF) lamp 33, which produces ultraviolet (UV) light within a bandwidth of approximately 100 nM to approximately 450 nM.

CCF lamp 34 is enclosed by a parabolic or spherical first-surface reflector 67 and a fixed enclosure window 65. UV rays, shown schematically as 34, generated by the CCF lamp 33 pass through the fixed enclosure window 65, and thereafter into the cleaning chamber lower section 36 through a second window 35 within which a cleaning and disinfecting solution 57 and one or more items of dental hardware are placed. The aqueous cleaning solution 57 is comprised, in part, of hydrogen peroxide ($H_2O_2$) in a concentration of between approximately 1% (10,000 parts per million (PPM)) to approximately 5% (50,000 PPM) in order to ensure proper disinfection of the dental hardware. Other constituents may also be components of the cleaning solution.

The illustration of the cleaning chamber as shown in FIG. 1 is intended to depict the major elements of this assembly for describing the general process itself. Additional details of the cleaning chamber are provided in FIGS. 2, 2A, 2B, and 2C. Further descriptions of these figures will be provided hereinafter.

Again with reference to FIG. 1, the cleaning chamber within which the aqueous cleaning solution and the dental hardware are placed is comprised of an upper section 37 and a lower section 36. Both sections are constructed in major part out of a thermoplastic material. The upper section 37 is domed, having a central flat circular segment about its vertical axis, and has a first surface reflective material 39A affixed to its interior surfaces for reflecting incident UV light rays. The cleaning chamber lower section 36 also has a first surface reflective material 39B affixed to its interior surfaces, similarly intended to reflect incident UV light rays. Lower section 36 is also constructed to include window 35 as an integral component. Both chamber sections join by friction fit 38 around their respective perimeters such that this friction fit creates a leak-tight seal, thereby preventing the aqueous cleaning solution 57 from leaking or otherwise escaping from the assembled cleaning chamber.

During operation, the UV light rays 34 emitted by CCF lamp 33 pass through the fixed enclosure window 65 and cleaning chamber window 35, irradiating the cleaning solution 57. Reflector 67, placed below CCF lamp 33, reflects all emitted light rays not propagating in such a direction to pass through cleaning chamber window 35. When irradiated by UV light in the bandwidth of approximately 100 nM to approximately 450 nM, each $H_2O_2$ molecule dissociates by photolysis into two hydroxyl radicals (OH), these radicals being very reactant with organic compounds, specifically reacting and thus destroying bacteria and viruses, producing a sterilizing action. The OH radicals recombine to form pure water, without any detrimental waste product. UV light photons 34 that are emitted by CCF lamp 33 and that are not adsorbed by any $H_2O_2$ molecules pass through the cleaning solution 57, striking reflective surface 39A of the upper cleaning chamber section 37 and are thereafter reflected back toward cleaning solution 57 for absorption. Any photons that are not absorbed by the cleaning solution 57 but pass through it in such a way to strike the sides of the lower cleaning chamber section 36 are similarly reflected back through the solution by reflective surface 39B. Unabsorbed photons that pass directly back through the cleaning chamber window 35 are re-reflected back through the window and again through the cleaning solution by reflector 67. Thus, in this device, any UV light, once emitted but not immediately adsorbed by any $H_2O_2$ molecule, is re-reflected back through the cleaning solution 57 in such a way to maximize this adsorption. The nature and design of the cleaning chamber is such that its interior surfaces, except for that of the lower section window 35, are configured to be fully reflective of UV light photons. The interior surfaces are intended to reflect these photons in such a manner that they are redirected through the cleaning solution in paths different from and random with respect to their incident paths.

Referring again to FIG. 1, 12-volt DC power is further supplied by conductors 26 and 27 to branching conductors 40 and 53. Conductor 40 further branches to conductors 41 and 42. Conductors 42 and 53 supply 12-volt power to a variable DC voltage regulator 44 through resistors 50 and 51 via conductors 47, 48, and 49. Resistor 51 is a user-changeable variable resistor, the function of which is to set the gate voltage of regulator 44, producing a DC voltage potential of between 0 and 12-volts between conductor 52 and ground conductor 56, depending on its placement position.

Conductors 52 and 56 supply the energization voltage to a multi-pole DC micro-motor 54, which has an eccentric weight 55 attached to its rotor. Micro-motor 54, which is similar to micro-motors found in pagers, is rigidly affixed to vibratable holding frame or housing 64, into which the cleaning chamber is placed. When energized, the rotating eccentric weight causes a dynamic imbalance, resulting in the micro-motor vibrating in a plane perpendicular to its rotor's axis of rotation, the vector of radial force produced continually changing its angular direction within this plane. This vibration is thereafter physically transmitted to the cleaning chamber through housing 64, thus vibrating the cleaning chamber and all contents within at the frequency generated by the rotating micro-motor. Micro-motor 54, the cleaning chamber and its contents, and housing 64 are mechanically isolated from CCF lamp 33, reflector 67, and CCF lamp enclosure window 65, as well as the remainder of the device, by an elastomeric vibration isolator 66. Vibration isolator 66 further serves as a perimeter light seal between windows 65 and 35, thus preventing UV rays from escaping to areas outside the device. Only the micro-motor 54 and its components, cleaning chamber and its components and contents, and housing 64 are vibrated. The remainder of the device, including all electrical circuitry and the CCF lamp and all associated components, remains stationary.

The rotational speed of micro-motor 54 is dependent upon the voltage supplied to it via conductors 52 and 56, this voltage in turn being dependent upon the placement position of the variable resistor 51. When positioned to result in a voltage potential of O-volts DC (between conductors 52 and 56), the micro-motor will not rotate, having no electrical energy to do so. As the variable resistor is repositioned to result in an increased voltage between conductors 52 and 56 (up to and including 12-volts), the micro-motor's rotational speed increases, corresponding to the voltage supplied to it. Micro-motor 54 is thus constructed in a manner that results in vibratory motion at frequencies ranging between of zero cycles per second (Hz) to greater than 20,000 Hz.

Referring again to FIG. 1, upon the energization of the device, branching conductor 41 and ground conductor 46 supply 12-volt power to light-emitting diode (LED) 43, resulting in the emission of indicating light 45.

Thus, when the cleaning chamber is correctly inserted within holding frame or housing 64, causing safety switch 60 to close, and subsequently when the momentary contact switch pushbutton 4 is depressed, the device is energized for the time period set by the user (by variable resistor 58), energizing CCF lamp 33 and vibrating micro-motor 54 for this time period. During this period indicator lamp 45 remains illuminated to indicate the energized state of the device to the user. At the end of the time period, an audible alarm automatically energizes, thereby alerting the consumer to the completion of the cleaning and disinfection cycle. It should be possible to clean and disinfect the dental hardware in as little as five minutes.

FIG. 1A illustrates a first option (Option I), according to which micro-motor 54 is positioned within the cleaning chamber lower section 36, it being affixed, encapsulated, or otherwise attached to or embedded within the cleaning chamber window 35. Electrical conductors for the micro-motor extend through the lower cleaning chamber side, terminating in electrical contact pads 88A and 88B. Electrical power from the main circuit is provided to micro-motor 54 by conductors 52 and 56, these conductors terminating in electrical contact pads 89A and 89B. When the cleaning chamber is correctly inserted within holding frame or housing 64, electrical continuity is created as electrical contact pad 88A mechanically contacts electrical contact pad 89A, and electrical contact pad 88B mechanically contacts electrical contact pad 89B, completing the electrical circuit through micro-motor 54.

According to a second option (Option 2) illustrated in FIG. 1A, an electrically conductive element 90 is embedded within or is otherwise affixed to the wall of the cleaning chamber lower section 36, this element terminating in electrical contact pads 91A and 91B, creating an electrical jumper. Conductors 9 and 59 are terminated in electrical contact pads 92A and 92B, replacing and eliminating switch assembly 60 (and components 61, 62, and 63, as illustrated in FIG. 1). When the cleaning chamber is correctly inserted within holding frame or housing 64, electrical continuity is created as electrical contact pad 91A mechanically contacts electrical contact pad 92A, and electrical contact pad 91B mechanically contacts electrical contact pad 92B, completing the electrical circuit.

In yet a further option (Option 3), illustrated in FIG. 1A, micro-motor 54 may be affixed, attached to, or encapsulated within the cleaning chamber upper section 37. In this option, electrical conductors 93 and 94 from micro-motor 54 are embedded within or are otherwise affixed to the cleaning chamber upper section 37, terminating in electrical contact pads 95A and 95B. Electrical power from the main circuit is provided to micro-motor 54 by conductors 52 and 56, these conductors terminating in electrical contact pads 96A and 96B. When the cleaning chamber is correctly inserted within holding frame or housing 64, electrical continuity is created as electrical contact pad 95A mechanically contacts electrical contact pad 96A, and electrical contact pad 95B mechanically contacts electrical contact pad 96B, completing the electrical circuit through micro-motor 54.

With reference to FIG. 2, the cleaning chamber is comprised of a lower section 69 and upper section 70, fitting together along their common perimeters via a friction fit 71. The chamber lower section 69 is also constructed to include a perimeter rib 78 that circumscribes it at its upper edge, and a bottom window 68 that is transparent to UV light. The upper chamber section 70 is partially domed but is constructed to include a circular flat 75. Both sections have first surface reflective materials 72A and 72B affixed to their interior surfaces, except for that of the lower section window 68. The upper section 70 is constructed to include two semi-circular extensions 76A and 76B near its lower edge, placed 180 degrees apart, while the lower section similarly includes two circular extensions 77A and 77B.

With reference to FIG. 2A, the first surface reflective material 72A is attached to the cleaning chamber upper section 70 via adhesive 73.

With reference to FIG. 2B, the first surface reflective material 72B is attached to the perimeter walls of the lower cleaning chamber section 69 by adhesive 74. Window 68 is molded or otherwise mechanically affixed to the cleaning chamber 69 as illustrated in order to create a leak tight joint.

With reference to FIG. 2C, the upper section 70 and lower section 69 of the cleaning chamber assemble via an interference friction fit. An extension of the upper section 70 fits inside the lower section 69 as shown, thus forming a leak tight perimeter seal at the junction of the sections. A perimeter rib 78 extends outward from the lower section 69 in order to strengthen the joint. Semi-circular extensions 76A and 77A extend outward from the bodies of the chamber sections as illustrated. First surface reflective material 72A is mechanically affixed to the upper cleaning chamber section 70 by adhesive 73, extending to the edge of the chamber itself. Similarly, first surface reflecting material 72B is affixed to the lower cleaning chamber section 69 by adhesive 74. This reflective material extends up on the sides of the chamber to such an extent so as not to interfere with the friction fit of the two sections as previously described.

With reference to FIG. 3, one illustrative embodiment of the fully assembled device is depicted. The assembled cleaning chamber 79 is properly and correctly inserted into the vibrating holding frame or housing 80, it being mechanically isolated from the remainder of the base unit 83 of the cleaning and disinfection system. Base unit 83, with cleaning chamber 79 fitted within holding frame 80, may be about 5 and ½ inches tall; 3 and ½ inches wide; and 4 inches deep. Housing 80 has two cut-outs placed diametrically opposite one another, one as shown 82, for the purpose of allowing for the correct positioning and placement of the cleaning chamber 79 and also for permitting the user to grasp and remove the cleaning chamber. The device includes, as was previously described, a momentary contact energization switch pushbutton 85, variable resistor 86 by which to alter the micromotor's rotational speed, and variable resistor 87 by which to set the energization time. Electrical power is supplied by cable 84. Retractable pivoting window 81 is included in the device as shown to cover and protect the device controls. Base unit 83, and possibly holding frame or housing 80, may be made of a clear, translucent, or semi-translucent colored plastic, as an eye-catching novelty. In this case the reflective material on the inside surfaces of cleaning chamber 79 and within base unit 83 should completely surround the entire combination of the ultraviolet lamp and the cleaning solution so as to prevent exposure of the consumer to potentially hazardous ultraviolet light.

Figure 4:
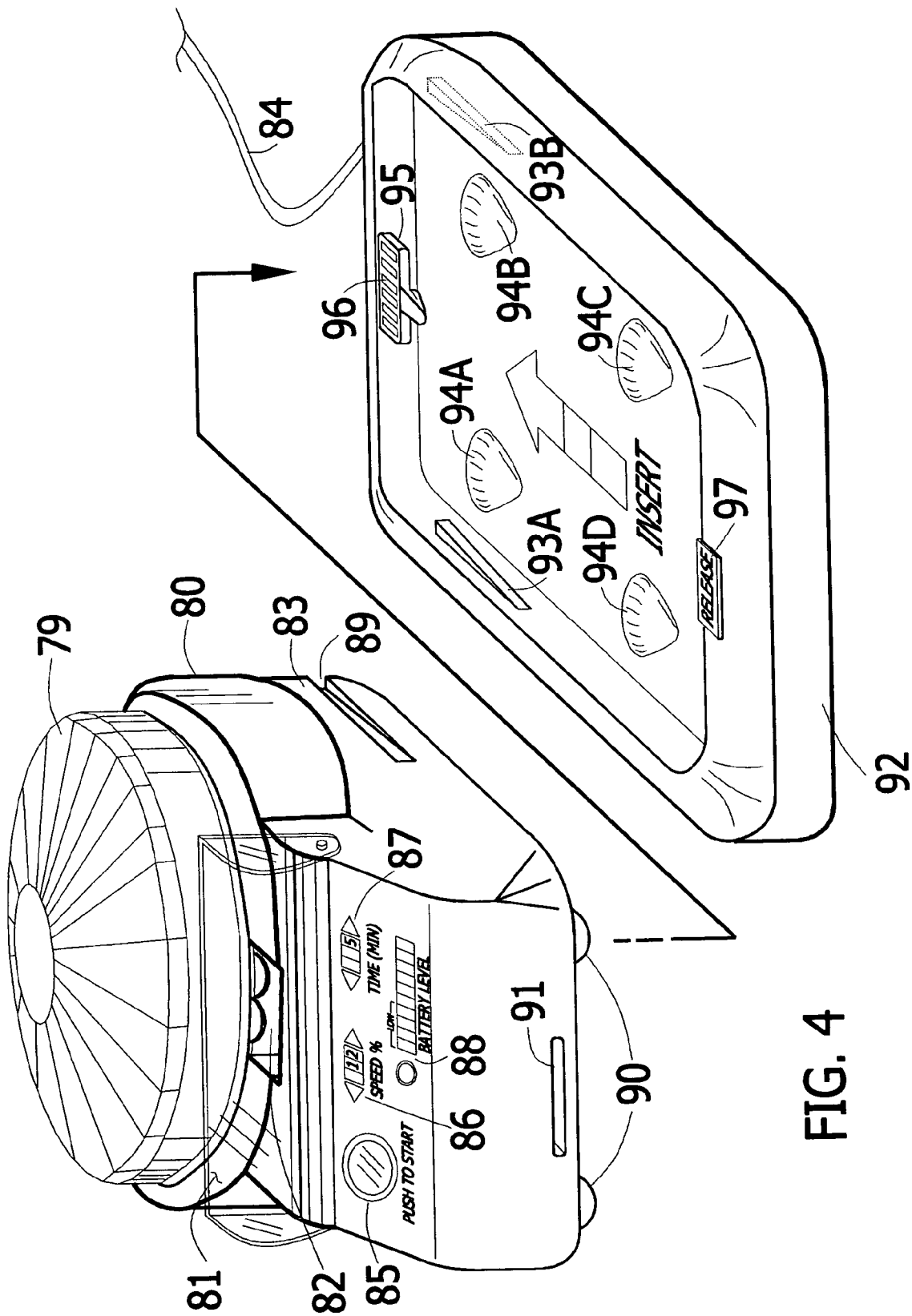
FIG. 4 is a drawing depicting an alternative option of a fully assembled cleaning and disinfection device in accordance with the invention.

With reference to FIG. 4, an optional, alternative illustrative embodiment of the fully assembled system is depicted. The system is assembled as previously described, except that base unit 83 is truncated in height. Base unit 83 includes a molded or manufactured tapered slot on each of its sides, one such slot 89 being illustrated, and four elastomeric button-type feet 90, symmetrically placed and affixed to the bottom of the base unit's lower panel. Two such feet are shown in the perspective view.

The system includes a docking station 92; within which are housed the AC electronics and AC-to-DC rectification components described above in connection with FIGS. 1-3. Thus, base unit 83 is foreshortened in height and includes within its enclosure a rechargeable DC battery pack.

Base unit 83 inserts into and mates with the docking station such that tapered wedge extension 93B (shown in phantom) inserts snugly by friction fit within slot 89, and tapered wedge extension 93A inserts into a similar slot (not shown) on the left-hand side of base unit 83, such that the wedges and slots act as molded keys and locks. Upon the insertion of base unit 83 into docking station 92 as illustrated by the "insert" arrow in FIG. 4, feet 90 will similarly mate with and reside within tapered hemispherical recesses 94A, 94B, 94C, and 94D. Additionally, upon the insertion of base unit 83 into docking station 92, male connector 95 with one or more electrical contacts 96 will similarly fit within and mate with a female electrical port at the rear of base unit 83. Upon the insertion of base unit 83 into docking station 92, a spring-loaded latch and hinged locking clip affixed to docking station 92 will extent into a mating slot 91 located on the face of base unit 83. When properly inserted, the base unit is held snugly in docking station 92 by wedge 93A and 93B and the clip inserted in slot 91. Removal of the base unit from the docking station is accomplished by depressing latch release button 97, which releases the clasp and clip inserted in slot 91, allowing the user to de-couple base unit 83 and withdraw it, in reverse fashion, from docking station 92.

In this embodiment and option, the system may be powered directly by an AC voltage source through power cable 84 when base unit 83 is mated to docking station 92. When de-coupled, the system may be powered directly by its internal battery pack, needing no external power source for operation.

To assist the user in establishing the condition of the battery pack's available energy level during remote use, a user-activated battery level indicator 88 is included in the device. Activation of the battery power level indicator is accomplished by momentarily depressing the small pushbutton adjacent to the display.

There have been described devices and methods for concurrently cleaning and disinfecting dental hardware utilizing UV peroxidation and subsonic, sonic, and ultrasonic vibration. It will be apparent to those skilled in the art that numerous additions, subtractions, and modifications of the described devices and methods are possible without departing the spirit and scope of the appended claims. For example, many different physical configurations of the base unit and cleaning chamber of the cleaning and disinfection system are possible, within the scope of the claims.

What is claimed is:

1. A method of cleaning and disinfecting for dental hardware, comprising:
   providing an at-home integrated cleaning and disinfection system for dental hardware, for consumer use, comprising a portable base unit sized for at-home use by a consumer, the base unit comprising a holding frame and an ultraviolet lamp, the system further comprising a cleaning chamber sized to fit within the holding frame and a vibration mechanism;
   providing a cleaning solution comprising hydrogen peroxide;
   placing dental hardware in the cleaning chamber;
   filling the cleaning chamber with the cleaning solution; and
   activating the vibration mechanism, to cause the cleaning chamber and contents therein to vibrate while the cleaning chamber is fitted within the holding frame, and activating the ultraviolet lamp, to expose the contents of the cleaning chamber to light emitted by the ultraviolet lamp.

2. The method of claim 1 wherein the base unit further comprises electronics and controls.

3. The method of claim 1 further comprising placing the cleaning chamber in the holding frame before activating the vibration mechanism and the ultraviolet lamp.

4. The method of claim 1 further comprising removing the cleaning chamber from the holding frame, as a portable storage container for the dental hardware.

5. The method of claim 1 wherein the vibration mechanism and the ultraviolet lamp operate simultaneously.

6. The method of claim 1 wherein the holding frame is a housing that surrounds the cleaning chamber circumferentially while the cleaning chamber is fitted within the holding frame of the base unit.

7. The method of claim 1 wherein the base unit, with the cleaning chamber fitted within the holding frame of the base unit, is about 5 and ½ inches tall; 3 and ½ inches wide; and 4 inches deep.

8. The method of claim 1 wherein the ultraviolet lamp of the base unit is positioned beneath the cleaning chamber while the cleaning chamber is fitted within the holding frame of the base unit.

9. The method of claim 1 wherein the ultraviolet lamp is a cold cathode fluorescent lamp.

10. The method of claim 9 wherein the cold cathode fluorescent lamp avoids substantial heating of the at-home integrated cleaning and disinfection system.

11. The method of claim 1 wherein the cleaning chamber comprises at least one internal reflector that reflects ultraviolet light into the cleaning solution.

12. The method of claim 1 wherein the base unit comprises at least one internal reflector that reflects ultraviolet light into the cleaning solution.

13. The method of claim 1 wherein the cleaning chamber comprises a transparent window through which ultraviolet light is transmitted from the ultraviolet lamp to the cleaning solution.

14. The method of claim 13 wherein cleaning chamber is removable from the holding frame and wherein the transparent window allows viewing of the dental hardware by the consumer without opening the chamber when the cleaning chamber is removed from the holding frame.

15. The method of claim 1 wherein the cleaning chamber comprises a lower section and a removable upper section in leak-tight friction-fit assembly.

16. The method of claim 1 wherein at least a portion of the base unit is mechanically isolated from vibration.

17. The method of claim 1 wherein the vibration mechanism is a micro-motor.

18. The method of claim 1 wherein an elastomeric seal between the cleaning chamber and the base unit restricts ultraviolet light from escaping from the system while the cleaning chamber is fitted within the holding frame.

19. The method of claim 1 wherein an audible alarm automatically energizes upon completion of a cleaning and disinfection cycle during which the vibration mechanism vibrates and the ultraviolet lamp is activated.

20. A method of cleaning and disinfecting for dental hardware, comprising:
   providing an integrated cleaning and disinfection system for dental hardware, comprising a base unit comprising a holding frame, an ultraviolet lamp, and a source of DC power electrically connected to the ultraviolet lamp, the system further comprising a cleaning chamber sized to fit within the holding frame, a vibration mechanism electrically connected to the source of DC power, and a docking station housing AC electronics and AC-DC rectification electronics;

mating the base unit with the docking station, the docking station powering the base unit;

separating the base unit from the docking station;

providing a cleaning solution comprising hydrogen peroxide; placing dental hardware in the cleaning chamber;

filling the cleaning chamber with the cleaning solution; and activating the vibration mechanism, to cause the cleaning chamber and contents therein to vibrate while the cleaning chamber is fitted within the holding frame, and activating the ultraviolet lamp, to expose the contents of the cleaning chamber to light emitted by the ultraviolet lamp, by DC power while the base unit is separated from the docking station.

* * * * *